United States Patent
Lehman et al.

(10) Patent No.: US 6,433,541 B1
(45) Date of Patent: Aug. 13, 2002

(54) IN-SITU METALIZATION MONITORING USING EDDY CURRENT MEASUREMENTS DURING THE PROCESS FOR REMOVING THE FILM

(75) Inventors: Kurt R. Lehman, Menlo Park; Shing M. Lee, Fremont; Walter Halmer Johnson, III, San Jose; John Fielden, Los Altos, all of CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 09/633,198

(22) Filed: Aug. 7, 2000

Related U.S. Application Data

(60) Provisional application No. 60/172,080, filed on Dec. 23, 1999.

(51) Int. Cl.$^7$ .......................... G01B 7/06; G01R 35/00; H01L 21/302

(52) U.S. Cl. ................... 324/230; 324/202; 324/207.12; 324/207.16; 324/225; 324/233; 324/234; 438/13; 438/17

(58) Field of Search ............................... 324/239, 230, 324/227, 234, 236, 260, 262, 202, 232, 207.12, 207.16, 207.18, 207.19, 225, 233; 438/13, 17

(56) References Cited

U.S. PATENT DOCUMENTS

| | | | | |
|---|---|---|---|---|
| 2,477,384 A | 7/1949 | Mann et al. | .................. | 175/183 |
| 2,564,777 A | 8/1951 | Cavanagh | ................... | 175/183 |
| 2,581,394 A | 1/1952 | Dinger | ......................... | 33/147 |
| 2,629,004 A | 2/1953 | Greenough | .................. | 175/183 |
| 2,686,039 A | 8/1954 | Bender | ........................ | 255/1.8 |
| 2,920,269 A | 1/1960 | Hanysz et al. | ................. | 324/34 |
| 3,400,331 A | 9/1968 | Harris | .......................... | 324/61 |
| 3,761,804 A | 9/1973 | Steingroever | ................ | 324/34 |
| 3,781,911 A | 12/1973 | Davidson | ...................... | 324/65 |
| 3,851,242 A | 11/1974 | Ellis | ............................ | 324/40 |

(List continued on next page.)

FOREIGN PATENT DOCUMENTS

| | | |
|---|---|---|
| DE | 4132562 A1 | 9/1991 |
| EP | 0581703 A1 | 2/1993 |
| EP | 0631147 A1 | 12/1994 |
| JP | 64-12277 | 1/1989 |
| JP | 5-149927 | 6/1993 |

OTHER PUBLICATIONS

D.Shenton and Z.J. Cendes, "Eddy, Current Analysis Of Thin Film Recording Heads," Mar. 15, 1984, American Institute of Physics.

Steven A. Henck, "In Situ Real–Time Ellipsometry For Film Thickness Measurement And Control," Jul./Aug. 1992, American Vacuum Society.

Bucknell, et al, "Interference Resonances in the Permeability of Laminated Magnetic Films," Oct. 15, 1990, American Institute of Physics.

*Primary Examiner*—Edward Lefkowitz
*Assistant Examiner*—Reena Aurora
(74) *Attorney, Agent, or Firm*—Beyer Weaver & Thomas, LLP

(57) ABSTRACT

Disclosed is a method of obtaining information in-situ regarding a film of a sample using an eddy probe during a process for removing the film. The eddy probe has at least one sensing coil. An AC voltage is applied to the sensing coil(s) of the eddy probe. One or more first signals are measured in the sensing coil(s) of the eddy probe when the sensing coil(s) are positioned proximate the film of the sample. One or more second signals are measured in the sensing coil(s) of the eddy probe when the sensing coil(s) are positioned proximate to a reference material having a fixed composition and/or distance from the sensing coil. The first signals are calibrated based on the second signals so that undesired gain and/or phase changes within the first signals are corrected. A property value of the film is determined based on the calibrated first signals. An apparatus for performing the above described method is also disclosed.

21 Claims, 12 Drawing Sheets

U.S. PATENT DOCUMENTS

| | | | |
|---|---|---|---|
| 3,878,457 A | 4/1975 | Rodgers | 324/34 |
| 3,986,105 A | 10/1976 | Nix et al. | 324/34 |
| 4,005,359 A | 1/1977 | Smoot | 33/0 |
| 4,266,187 A | 5/1981 | Slough | 324/65 |
| 4,358,338 A | 11/1982 | Downey et al. | 156/627 |
| 4,407,094 A | 10/1983 | Bennett et al. | 51/165 |
| 4,475,430 A | 10/1984 | Wright et al. | 324/61 |
| 4,564,810 A | 1/1986 | Geithman et al. | 324/230 |
| 4,567,436 A | 1/1986 | Koch | 324/230 |
| 4,602,981 A | 7/1986 | Chen et al. | 156/627 |
| 4,652,830 A | 3/1987 | Brown | 324/439 |
| 4,715,007 A | 12/1987 | Futjita et al. | 364/563 |
| 4,751,466 A | 6/1988 | Colvin et al. | 324/449 |
| 4,752,739 A | 6/1988 | Wang | 324/230 |
| 4,771,237 A | 9/1988 | Daley | 324/202 |
| 4,791,367 A | 12/1988 | Typpo | 324/229 |
| 4,845,421 A | 7/1989 | Howarth et al. | 324/61 |
| 4,849,694 A | 7/1989 | Coates | 324/230 |
| 4,893,079 A | 1/1990 | Kustra et al. | 325/225 |
| 4,942,545 A | 7/1990 | Sapia | 364/571.01 |
| 4,950,990 A | 8/1990 | Moulder et al. | 324/224 |
| 4,977,853 A | 12/1990 | Falcoff et al. | 118/665 |
| 5,001,356 A | 3/1991 | Ichikawa | 250/560 |
| 5,025,220 A | 6/1991 | Colvin et al. | 324/449 |
| 5,030,918 A | 7/1991 | Thon | 324/671 |
| 5,093,626 A | 3/1992 | Baer et al. | 324/671 |
| 5,122,743 A | 6/1992 | Blakeley et al. | 324/225 |
| 5,136,817 A | 8/1992 | Tabata et al. | 51/165.71 |
| 5,184,398 A | 2/1993 | Moslehi | 29/825 |
| 5,206,588 A | 4/1993 | Thorn | 324/230 |
| 5,242,524 A | 9/1993 | Leach et al. | 156/345 |
| 5,262,726 A | 11/1993 | Kohmura et al. | 324/232 |
| 5,278,500 A | 1/1994 | Seitz | 324/249 |
| 5,293,132 A | 3/1994 | Koch | 324/671 |
| 5,389,876 A | 2/1995 | Hedengren et al. | 324/242 |
| 5,399,968 A | 3/1995 | Sheppard et al. | 324/242 |
| 5,432,444 A | 7/1995 | Yasohama et al. | 324/240 |
| 5,442,286 A | 8/1995 | Sutton et al. | 324/242 |
| 5,510,709 A | 4/1996 | Hurley et al. | 324/242 |
| 5,552,704 A | 9/1996 | Mallory et al. | 324/233 |
| 5,559,428 A | 9/1996 | Li et al. | 324/71.5 |
| 5,606,260 A | 2/1997 | Giordano et al. | 324/339 |
| 5,617,024 A | 4/1997 | Simpson et al. | 324/209 |
| 5,629,621 A | 5/1997 | Goldfine et al. | 324/239 |
| 5,644,221 A | 7/1997 | Li et al. | 324/71.5 |
| 5,652,511 A | 7/1997 | Pearse et al. | 324/240 |
| 5,659,248 A | 8/1997 | Hedengren et al. | 324/242 |
| 5,660,672 A | 8/1997 | Li et al. | 156/345 |
| 5,663,637 A | 9/1997 | Li et al. | 324/71.5 |
| RE35,703 E | 12/1997 | Koch et al. | 324/230 |
| 5,731,697 A | 3/1998 | Li et al. | 324/71.5 |
| 5,754,043 A | 5/1998 | Logue | 324/207 |
| 5,770,948 A | 6/1998 | Li et al. | 324/226 |
| 5,781,009 A | 7/1998 | Lee et al. | 324/239 |
| 5,872,633 A | 2/1999 | Holzapfel et al. | 356/381 |
| 5,930,744 A | 7/1999 | Koch et al. | 702/170 |
| 5,939,880 A | 8/1999 | Logue | 324/232 |
| 5,948,206 A | 9/1999 | Inaba et al. | 156/345 |
| 6,040,695 A | 3/2000 | Raulerson et al. | 324/240 |
| 6,072,313 A | 6/2000 | Li et al. | 324/230 |

IN-SITU METALIZATION MONITORING USING EDDY CURRENT MEASUREMENTS DURING THE PROCESS FOR REMOVING THE FILM

CROSS REFERENCE To RELATED APPLICATIONS

This application claims priority of Provisional U.S. Patent Application, having Application No. 60/172,080 filed Dec. 23, 1999 entitled "IN-SITU METALIZATION MONITORING USING EDDY CURRENT MEASUREMENTS" by Lehman et al, which application is incorporated herein by reference in its entirety for all purposes.

BACKGROUND OF THE INVENTION

The invention relates to apparatus for performing measurements of film characteristics (e.g., film endpoint detection and thickness) of a semiconductor wafer during a fabrication process, such as chemical mechanical polishing (CMP) and chemical vapor deposition.

Two approaches to measuring a top-layer film thickness are the four-point probe and scanning electron microscopy (SEM) methods. The four-point method includes forming multiple contacts with the wafer surface to obtain a conductivity measurement. The SEM method includes cross-sectioning the wafer to thereby obtain the film thickness through common SEM imaging techniques. Although the four-point probe and SEM methods may provide adequate film measurements, these tests may only be performed on monitor wafers since these methods destroy the wafer during the measurement process.

One non-destructive measurement approach is to obtain optical measurements of the film thickness, e.g., via optical reflectance or transmission measurements. In-situ optical measurements are typically not performed during a CMP process because the sample undergoing polishing is obscured by debris that may adversely affect the measurement reading. The wafer is polished by rubbing the wafer between a wafer carrier and pad that is atop a platen. A slurry is typically used to mechanically and chemically facilitate removal of a portion of a film deposed on the wafer's surface. The CMP slurry and residues adjacent to the wafer surface are typically optically inhomogeneous and mostly opaque.

This debris (e.g., slurry and film residue) typically interferes with measurements of the sample. In a polishing process, it is desirable to detect when a film has been removed from the wafer, either entirely or to a specific thickness. When the film is removed, this is usually referred to as the endpoint. It is important to detect the endpoint so that the wafer is not over polished. For example, in copper CMP, the copper film is initially optically opaque. Typically, three endpoints are detected in copper CMP. A first endpoint may occur when the copper film is reduced to a specific thickness, which may be, for example, when the copper film begins to become optically transparent. Second, it is determined when the copper is completely removed so that the underlying liner layer (e.g., TaN or WN) is exposed. Finally, it is determined when the liner layer has been removed.

When the endpoint of a film is reached, the polishing can then be stopped without polishing away other structures on the wafer or to change process conditions. Since there is a lot of debris (e.g., slurry and/or film residue) associated with the CMP process, it would be difficult to accurately measure the endpoint while the wafer is undergoing CMP.

Although various approaches to performing in situ optical measurement during CMP have been proposed, none of these approaches solve the problem of debris obscuring the wafer. Of note, U.S. Pat. No. 5,433,651 describes a single beam reflectometer employing a window within a cavity of the CMP polishing pad and platen. The described approach has the disadvantage that CMP slurry and residue can build up in the cavity formed within the platen/polishing pad. The slurry and residue make optical measurements difficult. Another approach, described in E.P. Patent 96302176.1, attempts to solve this problem by providing a "soft window" within the cavity where slurry and residue might otherwise accumulate. Unfortunately, this window typically becomes scratched during the polishing process and pad conditioning and thereby also degrades the quality of optical measurements. Also, the material that is used to form the soft window typically scatters the measuring beam.

U.S. Pat. No. 5,081,796 describes moving a small edge portion of the wafer off the edge of the polishing pad, where the removed portion is then exposed to a jet of water which helps guide a beam onto the wafer's edge. However, this approach has the disadvantage of only measuring the film at the edge of the wafer. Since only a small portion of the entire wafer surface is measured, measurement of the endpoint is not very accurate. Furthermore, this procedure may adversely affect the polishing process.

An alternative approach to performing in situ optical CMP measurements is described in above referenced co-pending No. 09/396,143 (Attorney Docket No. KLA1P011) filed Sep. 15, 1999 entitled "APPARATUS AND METHODS FOR PERFORMING SELF-CLEARING OPTICAL MEASUREMENTS" by Nikoonahad et al, which application is incorporated herein by reference in its entirety for all purposes. Although this approach works well for measuring thin films, optical measurements are inadequate for measuring thick films.

Additionally, current approaches for estimating the duration for a film to be removed are inaccurate. That is, the polishing time tends to vary significantly from wafer to wafer. Thus, a significant amount of additional time is added to the polishing time estimate to account for wide variations in polishing time. Although this approach tends to assure that a film will be adequately removed, of course, this approach also adversely affects thorough-put.

Another non-destructive measurement technique utilizes an eddy current probe. One such technique is described in U.S. Pat. No. 6,072,313 by Li et al. This patent describes an eddy current probe that merely detects whether a film has changed. More specifically, the disclosed eddy current probe is formed from a high-Q tuned resonant circuit. This approach has several associated disadvantages. For example, the high-Q resonant circuits are sensitive to environmental changes, and therefore the eddy probe measurements are detrimentally affected by disturbances in environmental conditions, such as temperature, vibration, and changes in distances between the probe and the wafer. Additionally, only magnitude measurements at a single resonant frequency are provided. In sum, present approaches provide a relatively limited amount of information about the film under test.

Accordingly, there is a need for improved in-situ techniques and apparatus for providing information regarding a film while such film is undergoing a deposition or removal process. More specifically, there is a need for non-destructive techniques and apparatus for accurately and efficiently measuring film thickness and/or detecting a film's endpoint.

SUMMARY OF THE INVENTION

Accordingly, the present invention addresses some of the above problems by providing improved apparatus and methods for providing information regarding a film while such film is undergoing a deposition or removal process. Specifically, improved mechanisms for performing in-situ eddy probe measurements are disclosed.

In one embodiment, the invention pertains to a method of obtaining information in-situ regarding a film of a sample using an eddy probe during a process for removing the film. The eddy probe has at least one sensing coil. An AC voltage is applied to the sensing coil(s) of the eddy probe. One or more first signals are measured in the sensing coil(s) of the eddy probe when the sensing coil(s) are positioned proximate the film of the sample. One or more second signals are measured in the sensing coil(s) of the eddy probe when the sensing coil(s) are positioned proximate to a reference material having a fixed composition and/or distance from the sensing coil. The first signals are calibrated based on the second signals so that undesired gain and/or phase changes within the first signals are corrected. A property value of the film is determined based on the calibrated first signals.

In one aspect, the property value is a thickness value. In a specific implementation, the reference material is a sample carrier that holds the sample. Preferably, one or more third signals are measured in the sensing coil of the eddy probe when the sensing coil is not near any sample or reference materials, and calibration of the first signals is further based on the third signal. In one implementation, the calibration of the first signals results in compensation of gain and/or phase errors caused by a temperature change or a change in distance between the eddy probe and the reference material.

In another embodiment, a measurement device for obtaining information regarding a film of a sample is disclosed. The measurement device includes an AC voltage source and a sensing coil coupled with the AC voltage source so that the AC voltage source is operable to induce an AC voltage on the sensing coil. The measurement device also includes an impedance meter coupled with the sensing coil that detects a change in the AC voltage on the sensing coil, a memory having programming instructions, and a processor coupled with the memory. The processor and memory are adapted for causing the AC voltage to be induced on the sensing coil and analyzing the change in the AC voltage on the sensor to determine a thickness value of the film of the sample. In a specific implementation the processor and memory are further adapted to perform the above described methods.

In another aspect of the invention, a chemical mechanical polishing (CMP) system for polishing a sample with a polishing agent and monitoring the sample is disclosed. The CMP system includes a polishing table, a sample carrier arranged to hold the sample over the polishing table, and a measurement device as described above. The polishing table and sample carrier are arranged to receive a polishing agent between the sample and the polishing table and to polish the sample by moving the polishing table and the sample carrier relative to each other. The measurement device is arranged to obtain information regarding the sample while the sample is being polished.

These and other features and advantages of the present invention will be presented in more detail in the following specification of the invention and the accompanying figures which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF SPECIFIC EMBODIMENTS

Reference will now be made in detail to the specific embodiments of the invention. Examples of these specific embodiments are illustrated in the accompanying drawings. While the invention will be described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Since electrical resistivity is the inverse of electrical conductivity, determination of either of these quantities in accordance with the invention determines both of them.

Although for simplicity, the invention is described herein with reference to embodiments which determine a sample's electrical conductivity, it will be apparent to those of ordinary skill in the art how to implement variations on these embodiments to determine electrical resistivity in accordance with the invention. It will also be apparent to those of ordinary skill in the art how to implement variations on these embodiments to determine complex electrical conductance, resistance, sheet conductance, or sheet resistance. For example, electrical resistance can be determined by measuring electrical resistivity using the described apparatus, independently measuring a linear dimension of the sample by any conventional means, and dividing the measured resistivity by the measured linear dimension to determine the resistance. In the claims and the abstract, the term "conductance" is used in a broad sense to denote conductivity, resistivity, conductance, resistance, sheet conductance, or sheet resistance.

The expression "AC voltage" is used throughout the specification, including in the claims, to denote any periodically time-varying voltage, including for example, voltages having sinusoidal, square wave, or sawtooth waveforms.

In general terms, several embodiments of the present invention provide improved mechanisms for performing in-situ eddy current measurements and/or optical measurements. That is, the eddy current measurement apparatus and techniques of the present invention may be utilized alone or in combination with the optical apparatus and techniques of the present invention. Likewise, the optical apparatus and techniques of the present invention may be used with or without the eddy current apparatus and techniques.

Figure 1:
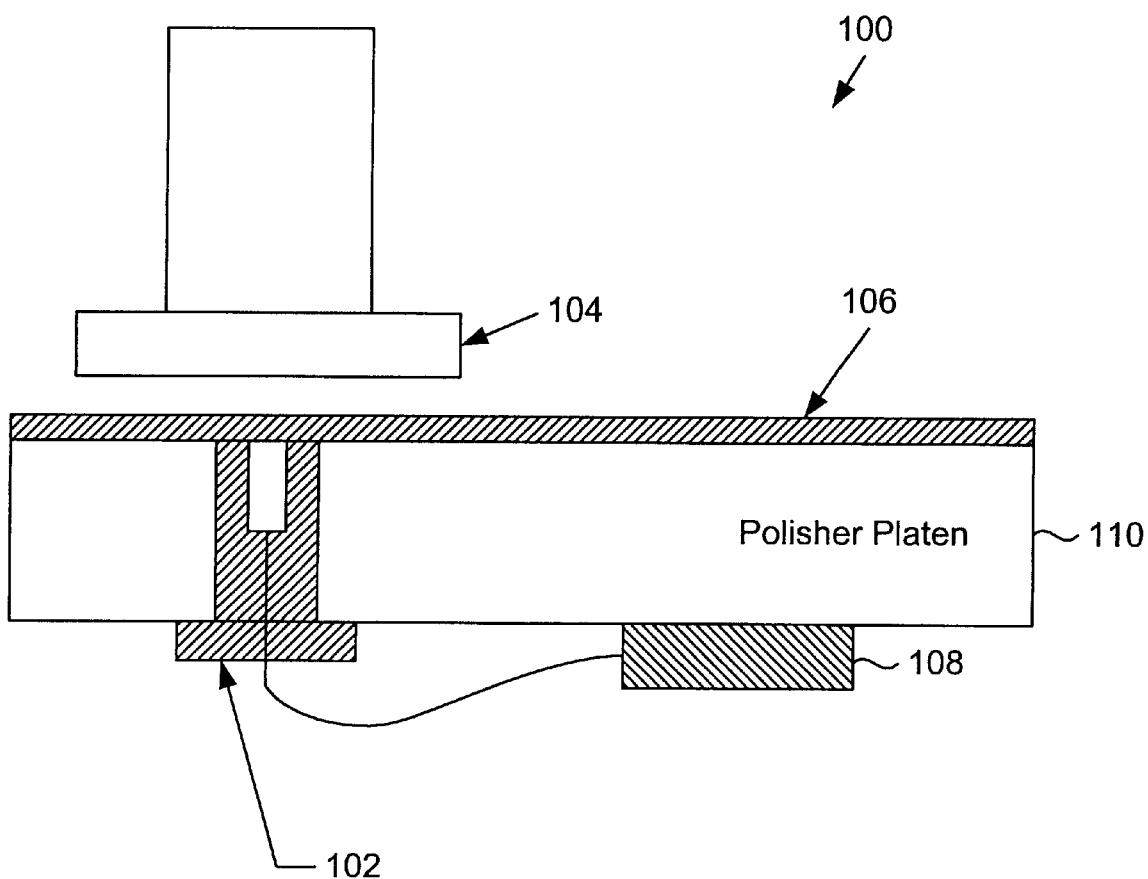
FIG. 1 is a diagrammatic representation of a chemical mechanical polishing (CMP) system having an eddy measurement device or probe in accordance with one embodiment of the present invention.

Referring initially to a novel eddy current system, FIG. 1 is a diagrammatic representation of a chemical mechanical polishing (CMP) system 100 having an eddy measurement device or probe 102 in accordance with one embodiment of the present invention. As shown, the eddy probe 102 is mounted within the polisher platen 110 beneath the pad 106. The CMP system 100 also includes a wafer carrier 104 to which a wafer may be mounted (not shown). As is well known to those skilled in the art, the platen 110 and pad 106 move relative to the wafer carrier to thereby polish the mounted wafer. As a result of such movement, the eddy probe 102 may obtain measurements of the wafer, wafer carrier, and/or free space as the platen 110 moves relative to the wafer carrier 10. As described below, eddy probe measurements of the wafer carrier and/or free space may be utilized to calibrate the eddy probe measurements of the wafer and thereby minimize environmental effects.

The eddy probe 102 is preferably coupled with processor 108 that includes a general purpose digital computer programmed with software for generating the data signals described herein (for example signals indicative of the below-described conductance function and related film thickness, and signals indicative of the below-described conductivity or resistivity values and related thickness values), and for storing data in (and retrieving stored data from) memory associated therewith. Of course, any suitable combination of hardware and/or software may be utilized for controlling the eddy probe 102 and analyzing signals measured by the probe 102.

The eddy probe circuit may be implemented in any suitable manner. In general terms, the eddy probe includes a sensing coil, an AC voltage source for inducing an AC voltage on the sensing coil, and an impedance meter for measuring an impedance or impedance change on the sensing coil. The impedance meter may take the form of any suitable meter for measuring the real and imaginary components of the sensing coil impedance. Alternatively, the impedance meter may include a bridge coupled with the sensing coil, as well as a reference coil, and a synchronous detector as described below with reference to FIG. 2.

Figure 2:
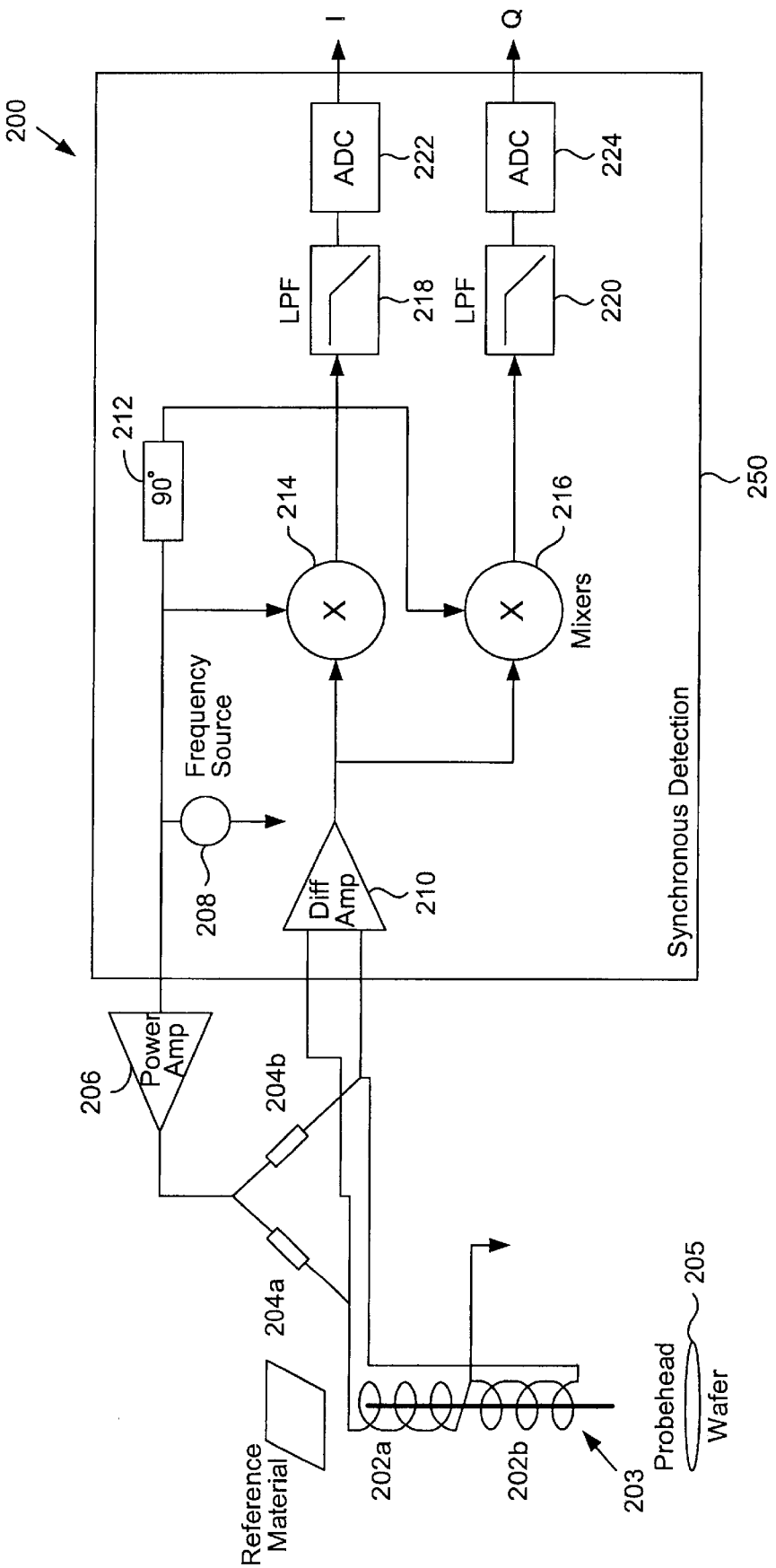
FIG. 2 is a simplified equivalent circuit of an eddy circuit in accordance with one embodiment of the present invention.

FIG. 2 is a simplified equivalent circuit of an eddy probe circuit 200 in accordance with one implementation of the present invention. The eddy probe circuit 200 includes differential probe coils 202 mounted within a probe head 203. The differential coils 202 include a sensing coil 202$b$ positioned close to the sample and a reference coil 202$a$ positioned away from the sample. In one embodiment, the probe head 203 is mounted within the platen of the CMP system (not shown). The eddy probe circuit 200 also includes an impedance bridge 204 coupled with differential probe coils 202. The impedance bridge 204 is also coupled with a synchronous detection block 250 for measuring the I and Q difference values of the differential probe coils 202. The differential probe coils 202 are also driven by frequency source 208 through power amp 206 and bridge 204.

When activated, frequency source 208 produces AC voltage in differential probe coils 202 with a selected frequency within the range from 1 KHz to at least 100 MHz. In a typical case in which differential probe coils 202 (and associated electrical lines) represent a load of 50 ohms to source 208, source 208 is capable of producing sinusoidal voltage having a peak-to-peak amplitude of about five volts in differential probe coils 202. To increase the probe's spatial resolution, thereby allowing measurement of the conductance of smaller sample regions (either at the sample surface or at selected depths below the sample surface), the diameters of differential probe coils 202 should be reduced and the AC voltage frequency in differential probe coils 202 increased. Additionally, the AC voltage frequency may be selected based on any suitable factor. For example, the frequency may be selected for different film thicknesses, material composition, probe-to-carrier distance, and/or probe size. A sweep of frequencies or several simultaneous discrete frequencies may also be selectably generated on the eddy probe.

Desired thin layers of a multilayer sample can be selectively measured because, for a given probe, the depth of the sample region measured depends in a well understood manner on the AC voltage frequency in differential probe coils 202. The differential coil voltage frequency can be chosen to cause the electromagnetic field due to the differential coil to extend to a desired depth in the sample.

For a given separation between the lower end of sensing coil 202$b$ and sample 205, the amplitude of the AC voltage induced in sensing coil 202$b$ in response to AC voltage in sensing coil 202$b$ will depend on the conductance of sample 205. Differential amplifier 210, which is connected to differential probe coils 202, amplifies the difference between the signals from the reference coil 202$a$ and the sensing coil 202$b$. By taking a difference between the reference coil 202$a$ and the sensing coil 202$b$, differences caused by environmental changes to the coils may be reduced since these changes, in theory, affect both coils about equally. Alternatively, a single probe coil could be used. This difference signal contains an in-phase component and the quadrature component. The output of the differential amplifier 210 is input into a first mixer 214, along with the AC voltage output from source 208. The output of the amplifier 210 is also input to a second mixer 216, along with the AC voltage that has first been phase shifted by 90 degrees. The output of mixer 214 is input to a low pass filter 218, and the output of mixer 216 is output to a low pass filter 220. The output of the low pass filters are the separated in-phase (I) and quadrature (Q) components of the differential probe coils 202. These signals are then sent through analog-to-digital converters 222 and 224, respectively, to generate digital I and Q values. Alternative methods for detecting I and Q components could also be used.

In order to provide high sensitivity to thin conducting films, it is desirable that amplifier 210 be selected to provide a high gain (on the order of 10,000 to 50,000). To avoid signal saturation, such high gains can only be used if the bridge circuit 204 is precisely balanced, so that the bridge voltage output is effectively near zero when no sample is present proximate the sensing coil 202b. As it is currently difficult to construct the differential probe coil assembly 202 such that the two coils are electrically identical, it is necessary to adjust the impedance of either the fixed bridge elements 204 or of the probe coils 202. The impedance of the fixed bridge or probe coils may be balanced by any suitable impedance adjustment mechanism. For example, a variable resistance may be added in series with either probe coil 202 or either bridge resistor 204. The imaginary impedance term may be balanced by placing a small capacitance across either probe coil 202 or either bridge resistor 204. The resistive and capacitive elements used to balance the bridge circuit just described may take the form of discrete components that are manually adjusted, or they may be replaced with active elements such as electronically variable resistors and variable capacitance diodes or varactors, which may be used to dynamically balance the bridge circuit either under computer control or via closed-loop control circuitry. Of course, if it becomes possible to construct the differential probe coil assembly 202 such that the two coils are electrically identical, it may become no longer necessary to adjust the impedance of either the fixed bridge elements 204 or of the probe coils 202.

Thus, the output signals from synchronous detection block 250, preferably a digital signal indicative of the amplitudes of both the in-phase and quadrature components of the induced voltage in differential probe coils 202, undergoes processing in accordance with the invention in processor 108 of FIG. 1 (in a manner to be described below). In sum, the in-phase and quadrature components of the induced voltage in differential probe coils 202 are measured using an AC mutual-inductance bridge. An alternative eddy current circuit is described in U.S. Pat. No. 5,552,704 by Mallory et al filed Jun. 25, 1993, which patent is herein incorporated by reference in its entirety.

The bridge design provides some protection against environmental changes to the probe during measurements. That is, the bridge is relatively immune to variable environmental conditions. In some preferred embodiments, each coil is wound on a core of material, such as a conductive epoxy or high permeability ferrite material, that also minimizes environmental effects and improves signal-to-noise. In other preferred embodiments, each coil is wound on a core of acrylic material. The differential probe and bridge design also provides a sensitive impedance measurement of the sensing coil 202b relative to the reference coil 202a. That is, the absolute impedance of the sensing coil 202b as affected by a sample may be obtained. In other words, there is a quantifiable measurement.

As explained below, the absolute impedance values can be directly correlated to absolute thickness values. Accordingly, precise removal rates may also be determined. Previous eddy probe methods are capable of only determining that thickness had changed, but are not capable of determining by how much the thickness has changed. That is, conventional methods cannot isolate the area of interest from environment induced changes. Thus, conventional methods required extensive calibration and priori knowledge of the process and sample.

Additionally, the probe 203 may be easily scaled down to obtain a small spot size. Thus, when the size of the differential probe is reduced, a smaller, but usable, signal may still be detected by the differential probe.

As described above, the eddy current measurement techniques of the present invention may be utilized in various types of in-situ applications. For example, an eddy current probe may be integrated within a chemical mechanical polishing (CMP) tool. In this application, the eddy current probe is utilized to detect one or more endpoint(s) of one or more etched layers. By way of another example, an eddy current probe may be integrated within a deposition tool. In this case, the eddy probe is utilized to detect film thickness of a deposited layer.

Turning first to the CMP application, techniques for determining film thickness of a sample undergoing CMP using an eddy probe are provided. These mechanisms may also be used to determine temperature and the distance between the probe and sample. In general terms, phase and magnitude measurements for the sample under test, sample carrier, and free space are obtained. The measurements of the sample carrier and/or free space may be utilized to calibrate the measurements taken of the sample under test. In general terms, the measurements of the sample carrier and/or free space (or open coil) are used to compensate for gain and phase errors within the measurements of the sample's film thickness.

The sample carrier is typically formed from a conductive material (encased in plastic) that surrounds the sample, and the composition and thickness of the sample carrier is expected to remain constant. Thus, a measurement of the sample carrier provides a stable reference point for continuously calibrating the measurement of the sample. The measurement of the reference also provides a mechanism for determining the distance from the probe to the carrier (e.g., as a measurement of pad thickness). Of course, any suitable reference material may be used, and the reference material may be placed at any measurable position. For example, a slug of conductive material may be mounted behind the wafer carrier. A measurement of free space provides a mechanisms for sensing changes to the detection circuitry (e.g., change in coil temperature, etc.).

Figure 3A:
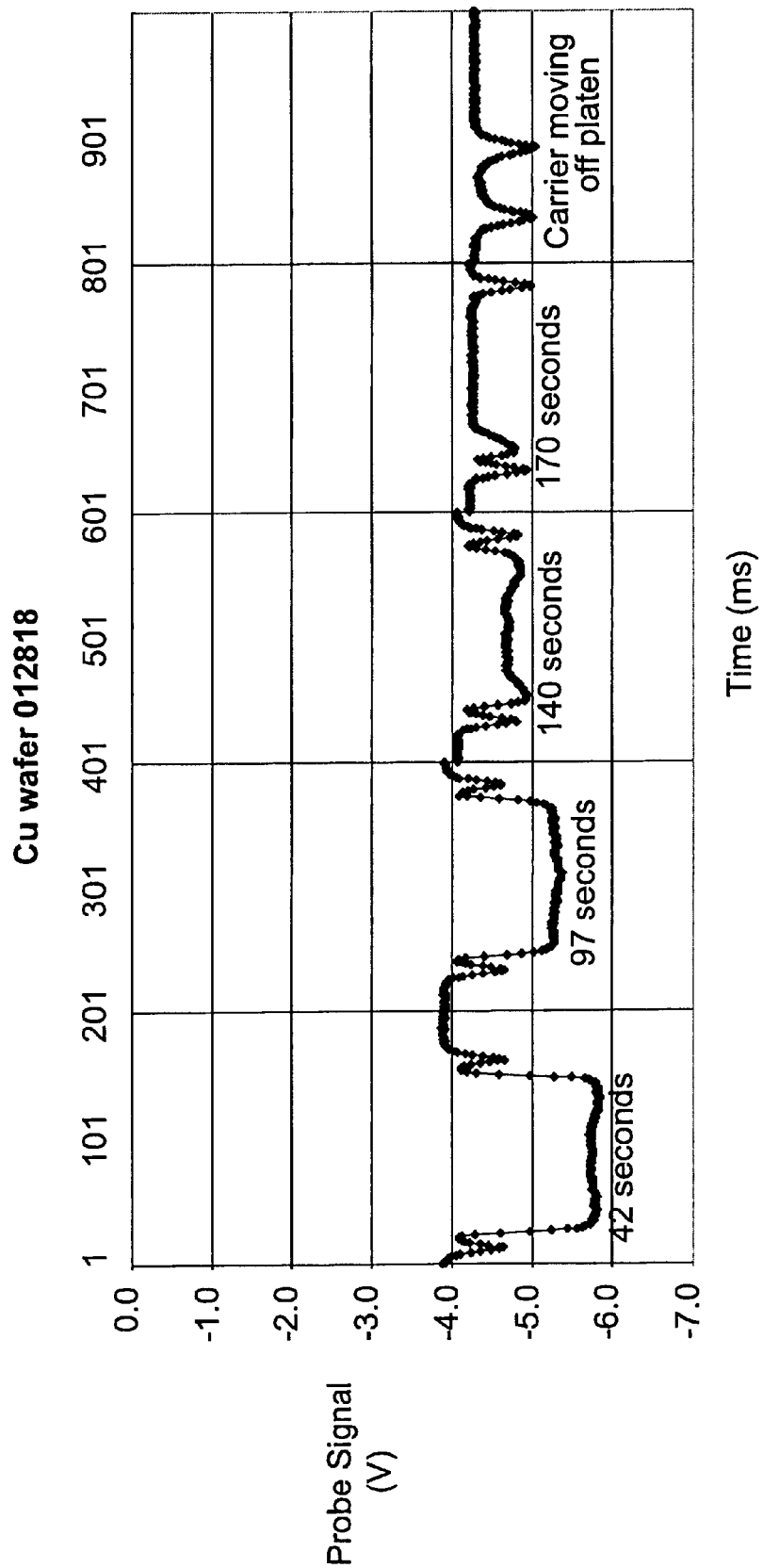
FIG. 3A is a graph of an output of the eddy probe of FIG. 2 as a function of time in accordance with one embodiment of the present invention.

FIG. 3A is a graph of an output of the eddy probe (e.g., real or imaginary component) of FIG. 2 as a function of time in accordance with one embodiment of the present invention. The probe moves relative to the wafer and wafer carrier so that measurements are sequentially and repeatedly taken across the wafer, wafer carrier, and free space. Preferably, the probe is positioned so that it moves radially across the wafer. Referring to FIG. 3A, measured peak signal values for the sample carrier are shown at data points 234, 434, and 634 (in this example, each data point is 1 ms). The peak signal values for free space (or open coil) are shown at data points 212, 412, and 612. The peak signal values for a center point on the sample are shown at data points 310, 510, and 710.

Reference vectors (e.g., for the carrier) may then be defined as:

$$\text{REF}(I, Q) = (R_i - OC_i, R_q - OC_q) \quad [1]$$

$R_i$ is the I component for the sample carrier signal, and $R_q$ is the Q component for the sample carrier signal. Likewise, $OC_i$ is the I component for the open coil or free space signal, and $OC_q$ is the Q component for the open coil or free space signal. The wafer vectors may then be defined as:

$$WAF(I, Q) = (W_i - OC_i, W_q - OC_q) \quad [2]$$

$W_i$ is the I component for the wafer signal, and $W_q$ is the Q component for the wafer signal.

By comparing the sample and reference measurements, variations due to temperature and probe-to-carrier distance (as well as other types of variation) can be largely removed from the final calibrated magnitude and phase values. For example, temperature changes cause the peak signal for the carrier signal to drift down over time. This change in signal resulting from a temperature change is subtracted out of the wafer peak signal by noting the drift in open coil and reference signals. Likewise, a change in probe-to-carrier distance will cause a change in the difference between the open coil and carrier peak signals. This change in signal may also be compensated in the wafer signal.

Since measurements are quickly obtained with the differential coil and bridge arrangement, the calibrated magnitude and phase values may be quickly generated "on-the-fly" during the Cow process. These calibrated values may then be analyzed to readily determine various characteristics regarding the sample.

Figure 3B:
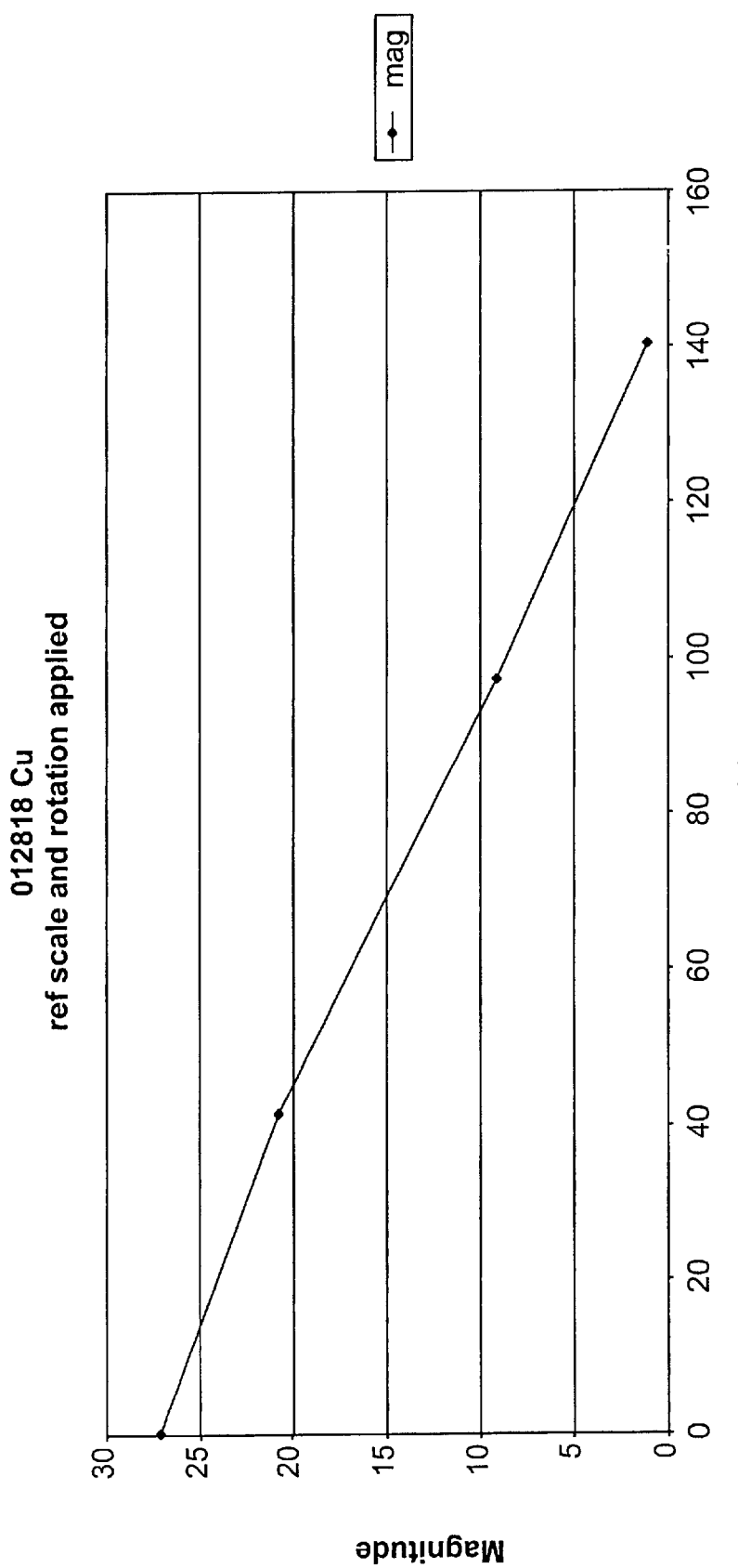
FIG. 3B is a graph of a calibrated magnitude output of the eddy probe of FIG. 2 as a function of time in accordance with one embodiment of the present invention.

FIG. 3B is a graph of a calibrated magnitude output of the eddy probe of FIG. 2 as a function of time in accordance with one embodiment of the present invention. The magnitude values (on the vertical axis) may then be easily converted to thickness values to generate a film thickness values as a function of time. For example, a sample having a known thickness value may be measured with the eddy probe to generate a linear function of thickness as a function of voltage. Alternatively, the thickness of a sample measured with the eddy probe may be determined with any suitable measurement system, such as a four-point probe. Magnitude/thickness vs. voltage graphs may be generated for multiple samples having known film thickness values and compositions. Thus, a measured voltage value from a sample having an unknown thickness may be correlated with a thickness value via thickness vs. voltage graphs.

Figure 3C:
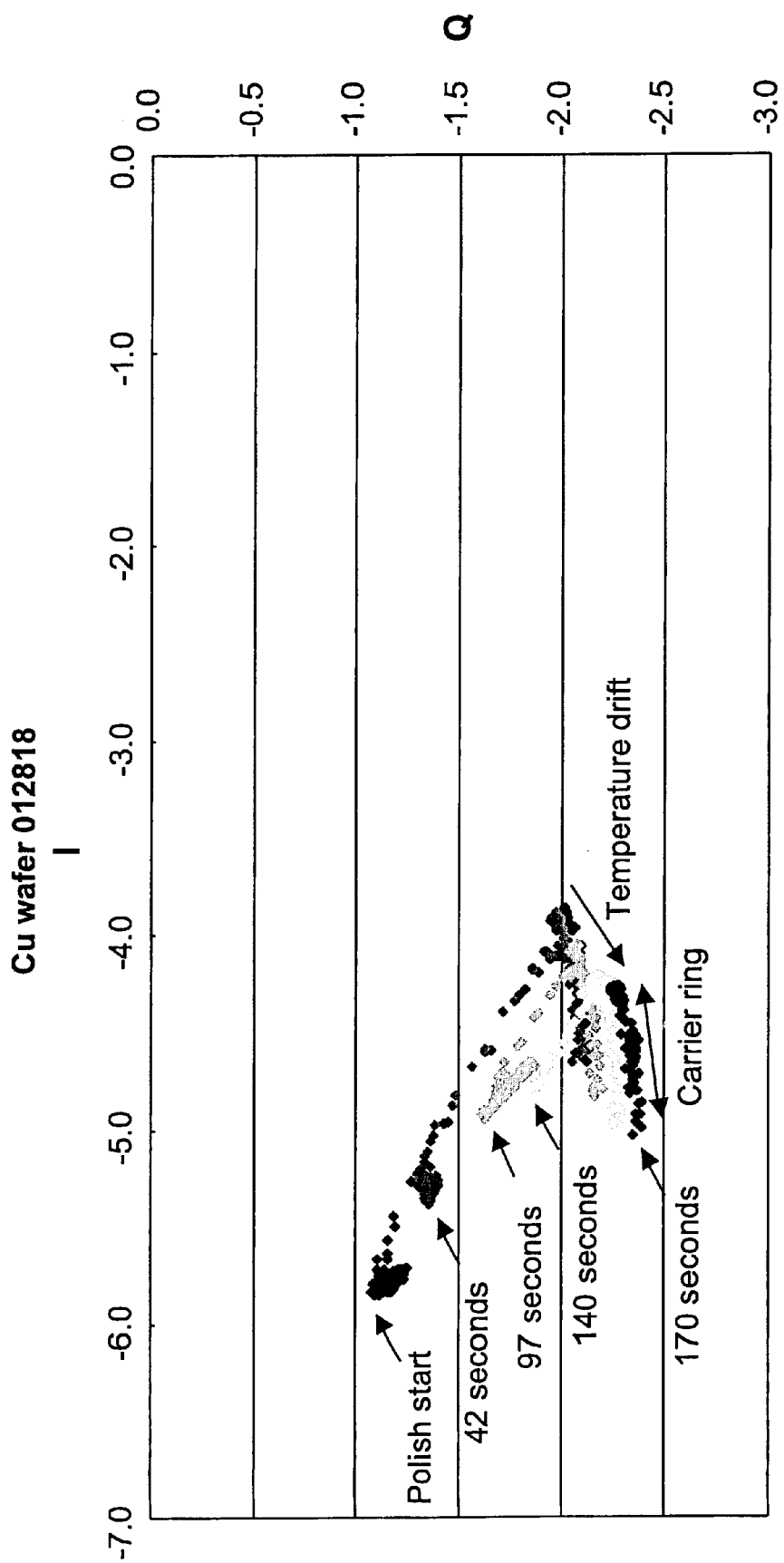
FIG. 3C is a vector plot of the measured voltage vectors (I vs. Q) of the eddy probe of FIG. 2.

A wealth of information is provided by measuring both the phase and magnitude at multiple positions (e.g., a carrier position, multiple wafer positions, and an open coil position). For example, the relationships between the different measured vectors (e.g., reference, wafer, and open coil vectors) may be graphically illustrated. For example, changes in the film thickness can be separated from changes in probe-to-sample distance and temperature effects by examining the real and imaginary changes in the probe coil impedance, along with the carrier and open coil measurements. FIG. 3C is a graph of each of the measured vectors (I vs. Q). Various environmental conditions cause the vectors to drift within the graph in a particular manner. As shown, a temperature change causes the vectors to move towards the origin point. In contrast, an increase in probe-to-carrier distance causes a decrease in the carrier signal's magnitude. The measurement vector direction is also affected by the material composition. For example, ferrous vs. non-ferrous metals may be easily discerned.

Changes in temperature and/or probe-to-sample distance values may indicate a problem within the CMP system. For example, a significant decrease in probe-to-carrier distance may indicate that the pad of the CMP system requires replacement. By way of another example, a significant increase in temperature may indicate that the CMP system is overheating and corrective action is required. The temperature change may also be used to estimate endpoint. For example, as copper is removed, the friction coefficient of the copper changes, which change results in a change in the amount of heat generated by the copper rubbing against the pad and slurry. This change in temperature may then be directly correlated with the endpoint.

Additionally, variations (e.g., variations in polishing rates, temperature, etc.) across the sample may also be determined during polishing and utilized to adjust the process on the fly (e.g., to maintain uniformity). For example, if one portion of the sample is polishing at a slower rate than the rest of the sample, adjustments to the polishing parameters may be made to increase the polishing rate to the slower polishing sample portion. The adjustment techniques depend on the particular configuration of the polishing system. For instance, air bladders may be mounted behind the sample carrier to provide back pressure to the sample against the pad. Pressure may be increased to a particular sample portion by increasing the air content of one or more bladders located behind the particular sample portion. Thus, film may be removed uniformly across the sample. Other types of CMP systems may simply provide air holes or vacuum holes behind the wafer for controlling pressure. In these configurations, the amount of air or vacuum is simply decreased or increased to particular sample portions based on the level of unevenness in polishing rates.

The use of time history and spatially diverse measurements across the sample (e.g., radial measurements of thickness) gives a fuller coverage and better confidence level for determining endpoints. One can use the time history to determine the polishing rate, and the remaining thickness to determine the endpoints. The radial non-uniformity can also be determined and accounted for in the prediction of endpoints and/or polishing rate. Hence, a relatively high confidence level for endpoint prediction is obtained.

The techniques of the present invention for monitoring various process parameters (e.g., temperature change, probe-to-sample distance, polishing rate, etc.) may be combined with any suitable conventional monitoring techniques. For example, techniques for monitoring motor current, torque, and motor ultrasonics may be used in conjunction with the techniques of this invention to more accurately adjust operating parameters of the CMP process.

Figure 3D:
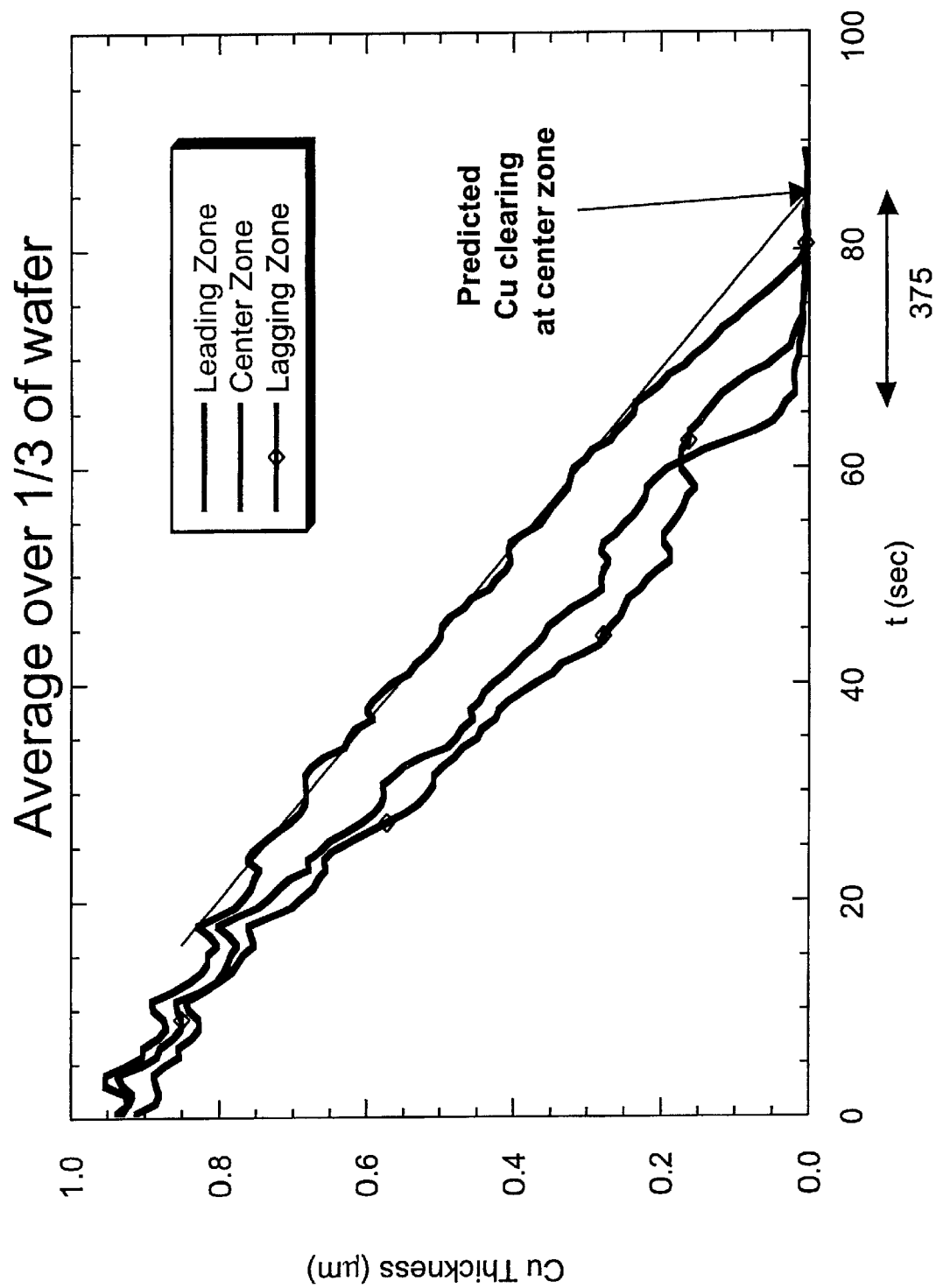
FIG. 3D is a plot of measured copper thickness vs. time during a polish process.

The reported variations in polishing rate may also be used to estimate the time required to reach a film's endpoint. For example, FIG. 3D illustrates three different polishing rates for three different sample portions. The difference in endpoints for each sample portion is depicted by arrow 375. A polishing time that is long enough to reach the endpoint for all three sample portions may then be selected (i.e., the longest polishing time).

Several eddy measurement analysis techniques are described in detail within U.S. Pat. No. 5,552,704 by Mallory et al filed Jun. 25, 1993, which patent is herein incorporated by reference in its entirety. This patent generally describes methods and apparatus for performing conductance measurements on a sample using an eddy current probe, without the need for measurement or knowledge of the separation between the probe and the sample. This eddy current analysis technique will next be described with reference to FIG. 4. Initially, look-up table data is generated (by operating processor 108) and the data is stored (in memory 108) as a look-up table for use in subsequent measurements on samples having unknown conductivity.

Figure 4:
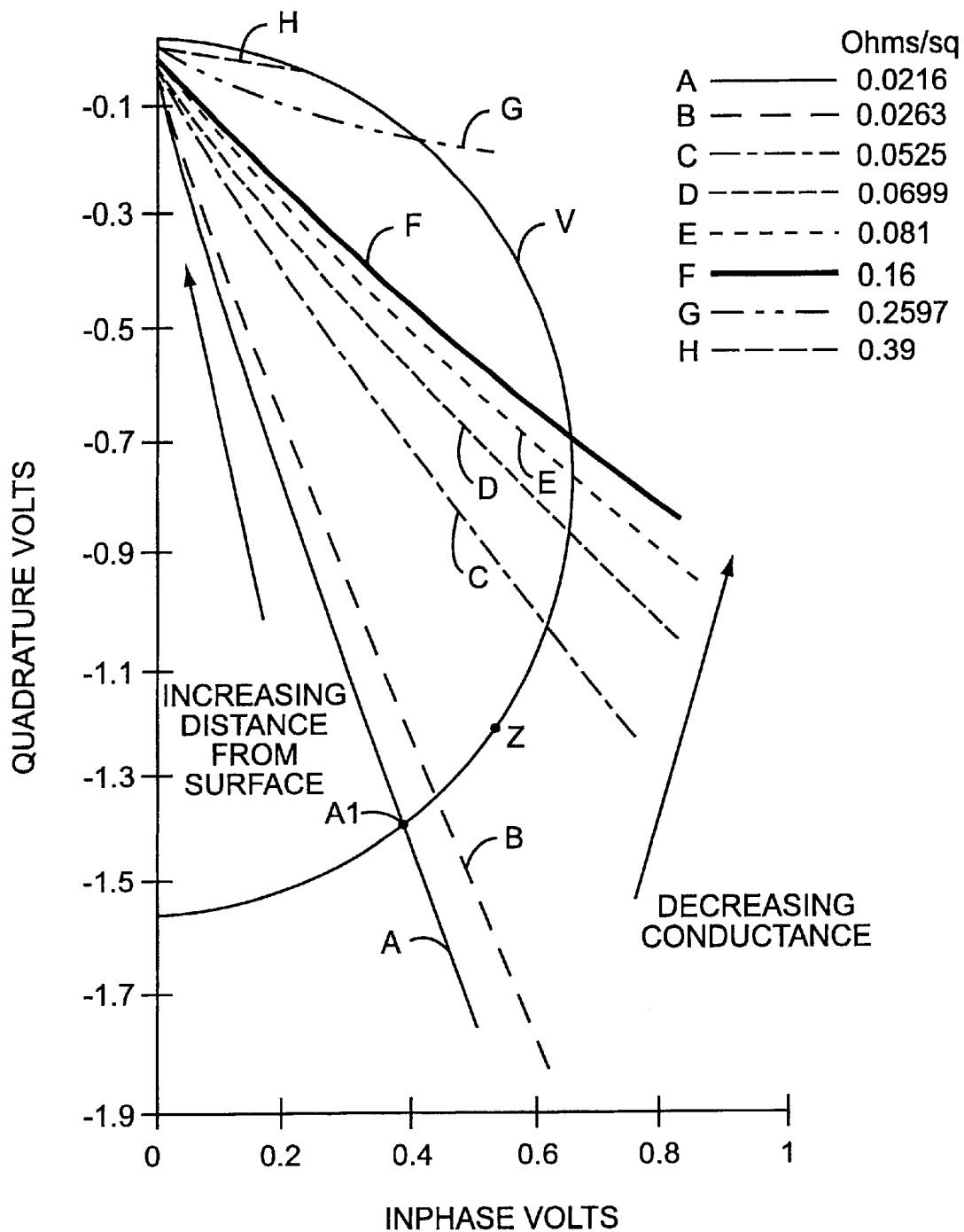
FIG. 4 is a graph of eight lift-off curves, and a circular arc intersecting the lift-off curves, generated in accordance with one embodiment of the present invention.

To generate the look-up table data, eddy current measurements are first performed on each of a number of samples (N samples) having known conductivity, to generate a corresponding number of lift-off curves (N lift-off curves). Eight such lift-off curves are shown in FIG. 4.

Each lift-off curve is generated by producing an AC voltage in differential coil 202 while measuring both the in-phase and quadrature components of the difference AC voltage induced in differential coils 202, for each of a number of probe positions along the z-axis. The separation between the sample and the probe (along the z-axis) need not be measured or otherwise known.

Typically, a small number (such as twenty-five) of coil voltage pairs (each pair comprising an in-phase difference voltage and a corresponding quadrature difference voltage) are measured for each sample. Each coil voltage pair is measured with a different probe position along the z-axis with respect to the sample. For each sample, a set of measured coil difference voltage pairs is processed to determine a lift-off curve.

Specifically, for a given sample, processor 108 processes an output signal from synchronous detection block 250 (indicative of a differential coil 202 voltage pair) for each of several probe positions to determine a polynomial function (a function of "in-phase" voltage versus "quadrature" voltage) which best fits the data. This function determines the lift-off curve for the sample.

An example of such a lift-off curve is the curve labeled "A" in FIG. 4. Lift-off curve A is determined by processing a number of sense coil voltage pairs (e.g., seven sense coil voltage pairs) obtained by measuring a sample having a known resistivity of 0.0216 ohms per square. Lift-off curve R is a graph of a polynomial function of form Y=–(K)–(L)X+(M)X.sup.2, where Y is quadrature voltage in units of Volts, X is in-phase voltage in units of Volts, and K, L, and M are constants. Processor 108 identifies this second order polynomial function as the one which best fits the measured voltage pairs.

In most cases, twenty-five (or a number on the order of twenty-five) sense coil voltage pairs are sufficient to characterize each lift-off curve with adequate precision. The range of probe positions (along the z-axis) over which measurements are made is proportional to the sample's conductivity (greater probe-to-sample separations are generally required for samples of greater conductivities), and depends also on the probe radius. As a rule of thumb (for a typical sample), the maximum probe-to-sample separation needed to determine a lift-off curve is substantially equal to 50% of the drive coil radius. We prefer to discard (or avoid measuring) sense coil voltage pairs for very large probe-to-sample separations, to avoid unnecessary processing of data that will not contribute significantly to an accurate lift-off curve determination.

Returning to the FIG. 4 example, each of lift-off curves A through H is determined by the same process employed to determine above-described curve A (one lift-off curve A through H for each of eight samples having a different known resistivity). The sample resistivities (in ohms per square) associated with curves A through H, respectively, are 0.0216, 0.0263, 0.0525, 0.0699, 0.081, 0.16, 0.2597, and 0.39.

After determining a set of reference lift-off curves (e.g., curves A–H shown in FIG. 4), processor 108 then determines a set of "intersection" voltage pairs, each intersection voltage pair representing the intersection of a different one of the reference lift-off curves with a "selected" curve (which can be, for example, a circular arc or another graph of a polynomial function) in X-Y voltage space, where X represents in-phase voltage and Y represents quadrature voltage. One such "selected curve" (circular arc V) is shown in FIG. 2. Selected curve V is a semicircle centered at X=0 volts and approximately Y=–0.8 volts. Alternatively, another selected curve could have been employed, such as a circular arc centered at the origin (Y=0 volts, X=0 volts). The "X,Y" coordinates of point A1 along lift-off curve A are an example of such an intersection voltage pair for "selected" curve V.

After processor 108 determines a set of intersection voltage pairs along a selected curve, processor 108 implements the next step of the inventive method which is to determine a functional relation between the known conductivity associated with each intersection voltage pair and the selected curve (referred to below as a "conductance function"). The conductance function determines a conductivity value for each point on the selected curve, including conductivity values not associated with any of the reference lift-off curves. For example, point Z on selected curve V corresponds to a unique conductivity (determined by processor 108 from the conductance function for selected curve V) that is greater than 0.0263 ohms per square (associated with lift-off curve B) and less than 0.0525 ohms per square (associated with lift-off curve C). In a class of preferred embodiments, processor 108 stores a conductivity value, determined by the conductance function, for each of many different points (index voltage pairs) on the selected curve in memory 108 as a look-up table. Each such conductivity value can be retrieved from the stored look-up table by accessing the memory location indexed by the corresponding index voltage pair.

In variations on the described method, a conductance function relating a known conductance (rather than a conductivity) of each measured sample to an intersection voltage pair on the "selected" curve, or a "resistance function" or "resistivity function" relating a known resistance or resistivity of each measured sample to an intersection voltage pair on the "selected" curve, can be determined and processed as a substitute for the above-described conductance function. For convenience, the expression "conductance function" is used herein (including in the claims) in a broad sense to denote any such conductance function, resistance function, or resistivity function, or any function which relates a known conductance, conductivity, resistance, resistivity, sheet resistance, or sheet conductance of each of a set of measured samples to an intersection voltage pair on a "selected" curve, as well as a narrowly defined conductance function (relating a known conductance of each of a set of measured samples to an intersection voltage pair on a "selected" curve).

Although the eddy probe is preferably located within the platen, it may also be located within the backside of the sample carrier. In this arrangement, the carrier no longer provides a reference signal. Thus, a temperature sensor is also preferably mounted to the carrier so that the measured sample signals may be calibrated for any temperature changes. A reference metal slug (encased in plastic) may also be positioned to periodical move past the probe so that a reference signal for a known sample may be obtained. In this configuration, the bridge probe design also allows relatively small spot size measurements, as compared with a resonator probe design.

Figure 5:
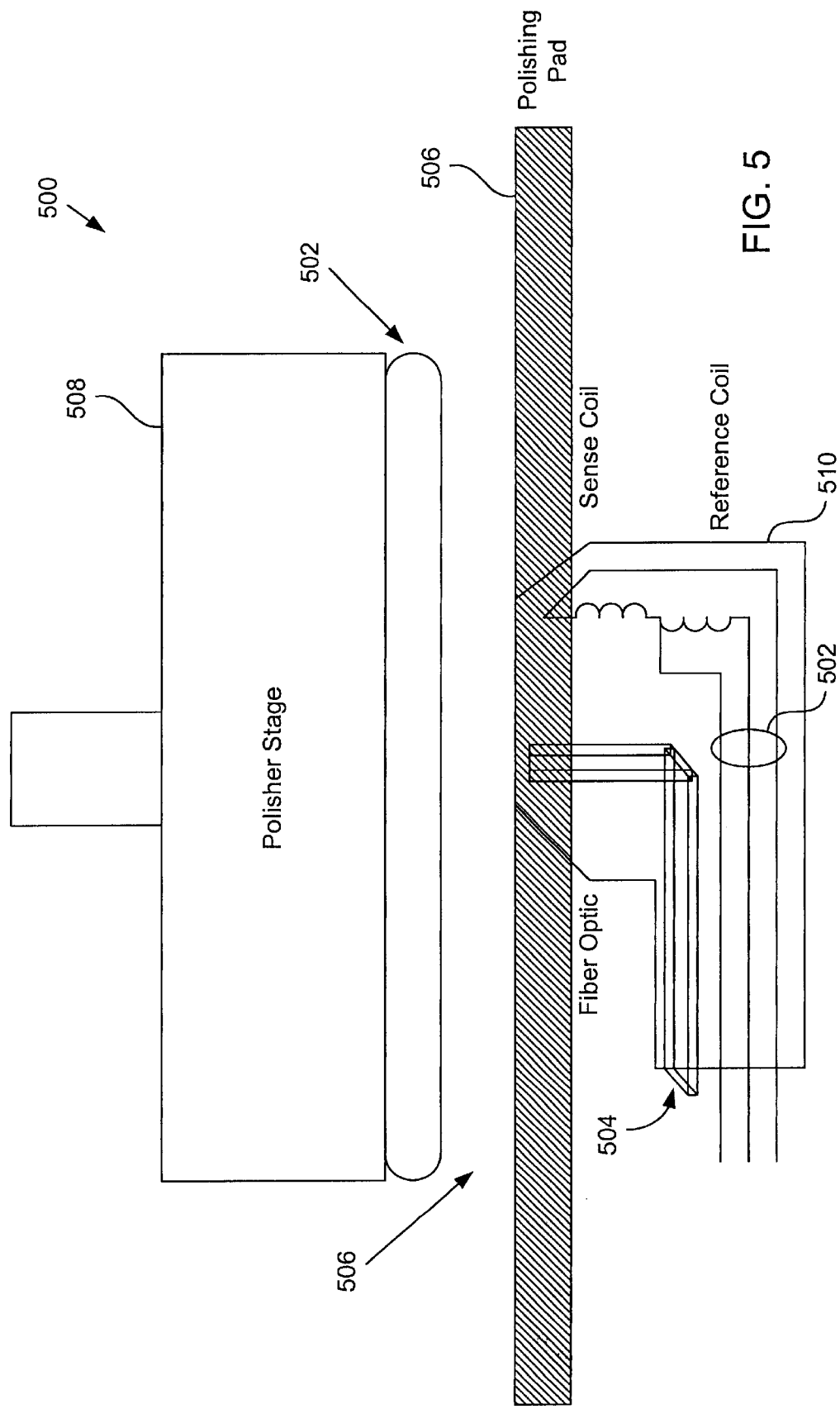
FIG. 5 is side view of a combination eddy current and optical measurement device in accordance with another embodiment of the present invention.

The CMP system may also include any suitable optical measurement device, in addition to the eddy probe. Since eddy current measuring devices work well with thick films and optical measuring devices work better with thin films, a broad range of film thickness may be measured by combining an eddy device and an optical device. FIG. 5 is side view of a combination eddy current and optical measurement device 500 in accordance with another embodiment of the present invention. As shown, the combination measurement device 500 is integrated within a CMP tool. In the illustrated embodiment, a fiber optic measuring device 504 and a eddy current probe 502 (e.g., as described above) are housed within housing 510. Housing 510 is formed from a material that is substantially transparent the eddy current signals and optical signals. For example, the housing is formed from glass.

The optical device may be integrated within the CMP tool in any suitable fashion so that accurate optical measurements may be obtained. For example, the eddy probe coils may be wrapped around the optical element. Preferably, the optical measurement device is positioned separately within the platen from the eddy probe system. Alternatively, the eddy probe may be positioned behind the wafer as described above. In one embodiment, a self-clearing objective is inserted within the platen and pad of the CMP tool for the optical measurement device. Optical measurements may be made through the self-clearing objective during CMP operation. Several embodiments of the self-clearing objective is described in the above referenced co-pending U.S. patent applications, Ser. No. 09/396,143 filed Sep. 15, 1999 entitled "Apparatus and Methods for Performing Self-Clearing Optical Measurements" by Nikoonahad et al. and No. 09/556,238 filed Apr. 24, 2000 entitled "Apparatus and Methods for Detecting Killer Particles During Chemical Mechanical Polishing" by Nikoonahad et al. These applications have assignment rights in common and are incorporated herein in their entirety.

Figure 6:
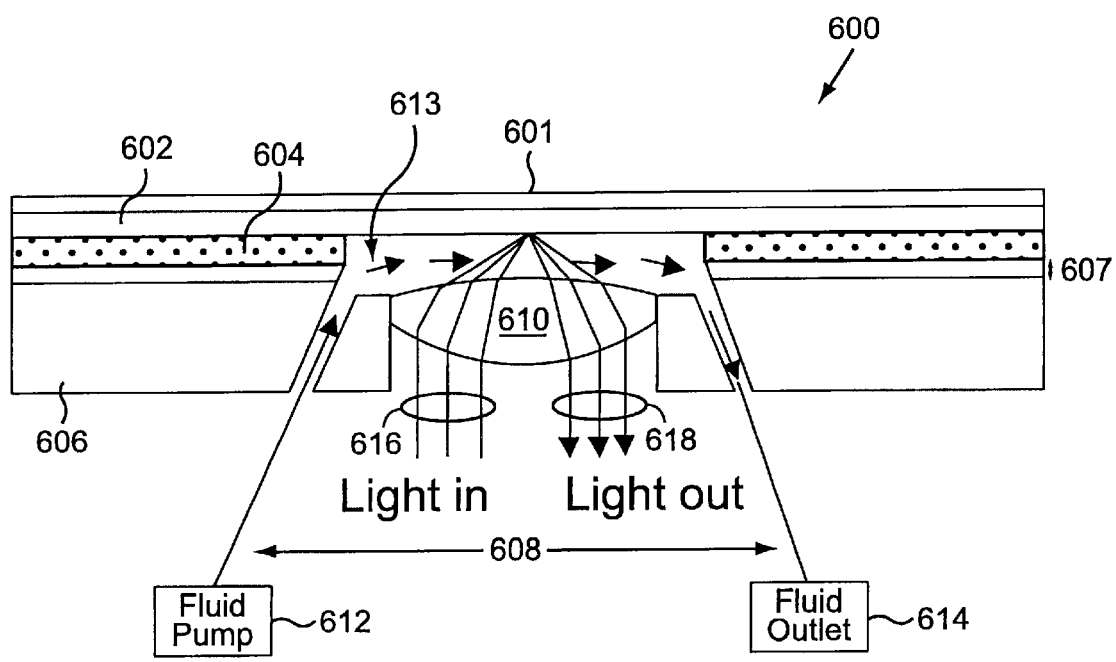
FIG. 6 is a diagrammatic representation of a section of a chemical mechanical polishing (CMP) apparatus that incorporates one or more measurement system(s) (not shown) with a self-clearing objective in accordance with one embodiment of the present invention.

FIG. 6 is a diagrammatic representation of a section of a chemical mechanical polishing (CMP) apparatus 600 that incorporates one or more measurement system(s) (not shown) with a self-clearing objective in accordance with one embodiment of the present invention. The dimensions of the various components are exaggerated to better illustrate the self-clearing objective of this invention. As shown, the CMP apparatus 600 includes a sample holder 601 and a pad 607 and a platen 606 having a hole 608. The sample holder 601 is arranged to hold a sample 602 against the pad 607 and the platen 606. A slurry 604 is placed between the sample 602 and pad 607, which is atop platen 606. When the sample is moved relative to the pad 607, the slurry 604 functions to mechanically and/or chemically polish the sample 602. Of course, any suitable polishing agent may be utilized.

The hole 608 of the pad 607 and platen 606 is configured to contain a self-clearing objective. The self-clearing objective of FIG. 6 includes an optical element 610 and a flowing fluid 613. Any suitable mechanism may be implemented for generating the flowing fluid 613 of the self-clearing objective. As shown, the self-clearing objective also includes a fluid pump 612 and a fluid outlet 614 that generate a constant fluid flow between the optical element 610 and sample surface 602. Alternatively, a fluid pumping system may be implemented within a single device that generates flowing fluid 613. By way of a final example, a ring-shaped hole may be formed around the viewing area into the center of which the fluid is pumped. The fluid then exits through the ring-shaped hole.

The fluid pump 612 may include a control valve (not shown) for adjusting the flow rate. Likewise, the fluid outlet 614 may include a vacuum that provides some control over the fluid flow rate to the fluid outlet 614. The fluid flow rate may be adjusted for different applications or polishing conditions in order to provide different levels of clearing depending upon the specific application. For example, the fluid flow rate may depend on type of slurry, polishing speed, size of fluid reservoir, configuration of optical element, wavelength of light, concentration of slurry, amount of impact on the process, etc. As shown, a slurry 604 that is placed between the pad 607 and the sample 602 is substantially cleared away from the viewing surface of the sample 602 by the flowing fluid 613.

The fluid pump 612 may also include a sensor (not shown) arranged to determine when the sample is near the self-clearing objective. The sensor may utilize pressure, optical, or other inputs to determine sample location. The fluid flow may then be modulated as the sample is near or on top of the self-clearing objective. This arrangement clears the debris along the optical path without overly diluting the slurry adjacent to the self-clearing objective. This prevents the slurry from becoming too diluted to effectively polish the sample.

One or more measurement signals 616 may be directed through the optical element 610 and the flowing fluid 613 to the sample 602 to be reflected, detected, and analyzed. One or more detectable signals 618 are then reflected from the sample 602. The measurement and detectable signals 616 and 618 are not significantly distorted by the slurry 604, as compared to other in-situ measurement systems, since the slurry 604 is cleared away from the signal path by fluid 613 of the self-clearing objective.

Any suitable type and number of optical measurement device may be used in conjunction with the self-clearing objective 600. By way of specific examples, a reflectometer system, an ellipsometer system, an interferometer system, and a photoacoustic system may be used. The optical measurement device may be configured in various ways. The reflectometer may measure reflectivity using multiple incident beam angles or a single beam angle. Additionally, the reflectometer may measure reflectivity at various wavelengths or a single wavelength. Likewise, the ellipsometer may be configured to measure at any combination of multiple angles, a single angle, multiple wavelengths, and a single wavelength.

Several reflectivity measurement apparatus and reflectivity analysis techniques are described in U.S. Pat. No. 5,747,813 by Norton et al and U.S. patent application Ser. No. 09/298,007 filed Apr. 25, 1999 by Wang et al. Several embodiment of ellipsometer apparatus and methods are described in U.S. Pat. No. 5,910,842 by Piwonka-Corle et al. Photoacoustic systems and methods are described in U.S. application Ser. No. 09/028,417 filed Feb. 24, 1998 by Nikoonahad et al. These patents and patent applications are herein incorporated by reference in their entirety.

Figure 7:
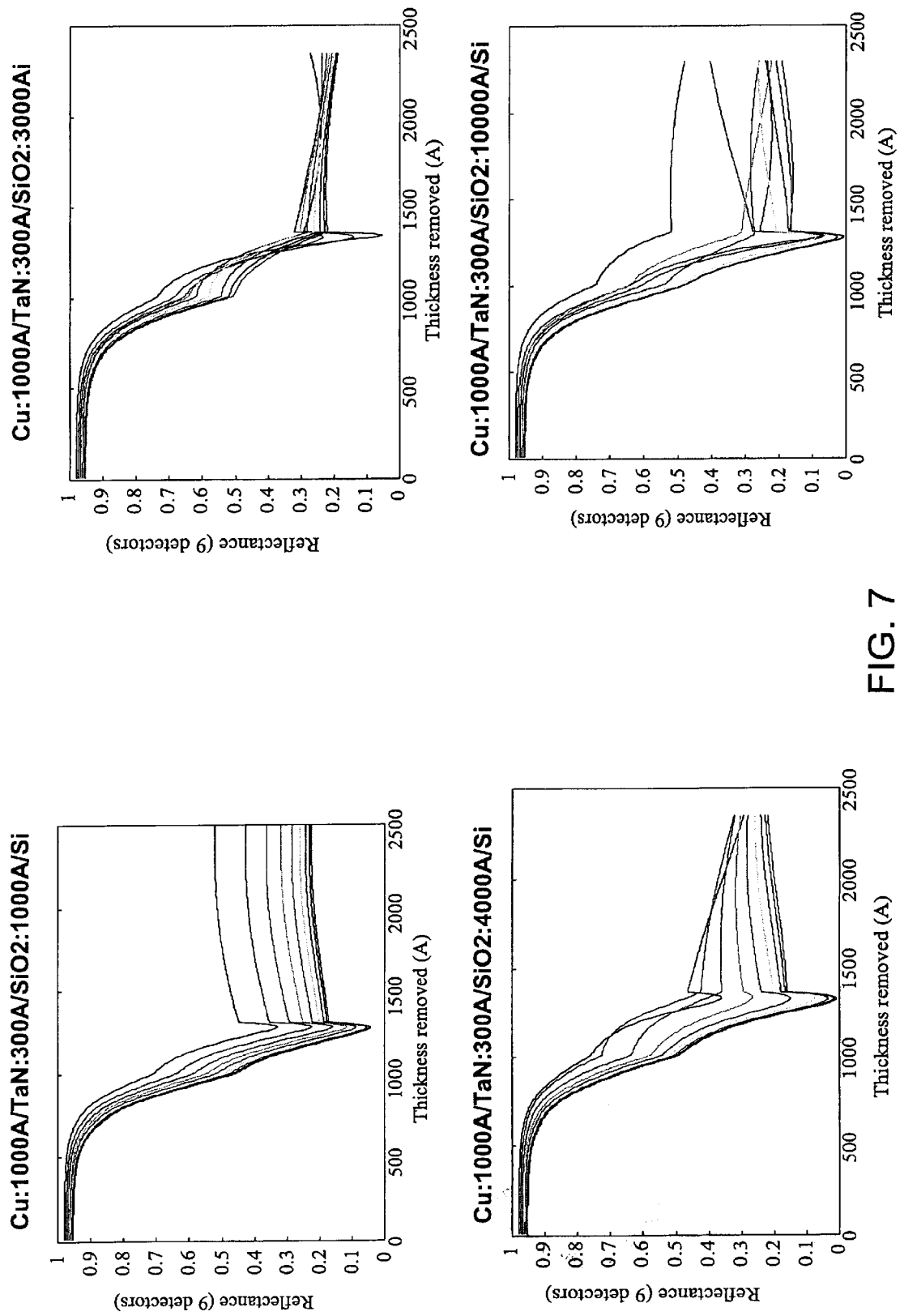
FIG. 7 shows four graphs of reflectivity values as a function of film thickness.

The optical measurement device may also be utilized to predict the endpoint time. It has been found that there is a dip in reflectivity when the endpoint is near. FIG. 7 shows four graphs of reflectivity values as a function of film thickness removed. As shown, there is a dip in reflectivity present when the film is completely removed. For example, there is a dip prior to removal of a 1000 Angstroms thick copper layer, and another dip present prior to removal of both 1000 Angstroms of copper and 300 Angstroms of TaN. Multiple reflectivity curves may be generated for various film thicknesses and compositions and operating conditions to determine how long after the reflectivity dip the endpoint occurs. For example, the endpoint may occur 5 seconds after the dip. One may then polish a little longer than the estimated 5 seconds (e.g., 10 seconds) to ensure that the endpoint is reached. Preferably, reflectivity is measured at several angles of incidence so that the dip may be more readily perceived.

This reflectivity dip provides a readily identifiable marker for estimating the time until endpoint is reached. This estimation procedure represents an improvement over conventional estimations of the entire polishing time from polish start to endpoint. Since it is unlikely that the polishing process will follow a same rate during the entire polishing process, a total polishing time estimation is unlikely to be accurate. In contrast, estimating the remaining polishing time after the dip is likely to be an accurate indicator of endpoint time since the rate is unlikely to change a significant amount in such a short amount of time until the endpoint is reached. The above described techniques for determining variations in polishing rate with the eddy probe may also be used with the reflectivity dip to determine endpoint. That is, extra time may be added to account for variation in polishing rates across the wafer. For example, extra time may be added to ensure that the slowest polishing wafer portion reaches endpoint.

Any suitable optical measurement device may be utilized to obtain multiple angles of incidence. Several embodiments of optical systems having multiple angles of incidence are described in the above-referenced co-pending U.S. patent application Ser. Nos. 09/396,143 and 09/556,238 by Nikoonahad, which are incorporated by reference.

Measurements may be taken with both the eddy current probe 502 and optical probe 504 to optimize film thickness measurement accuracy. That is, measurements are taken with both probes to obtain optimum results over a wide range of film thickness. For example, the eddy and optical probes together provide a complete range of metallization endpointing. It has been found that eddy probe measurements are sensitive to thicker film measurements, such as 200 to 400 Å or higher. It has also been found that optical measurements are sensitive to a top layer Cu thickness of about 400 Å to 500 Å or lower. Thus, eddy probe measurements may be utilized for thick film measurements, while optical probe is utilized for thin film measurements. Additionally, it appears that the eddy probe is relatively insensitive to the underlying film patterns on a sample.

Figure 8A:
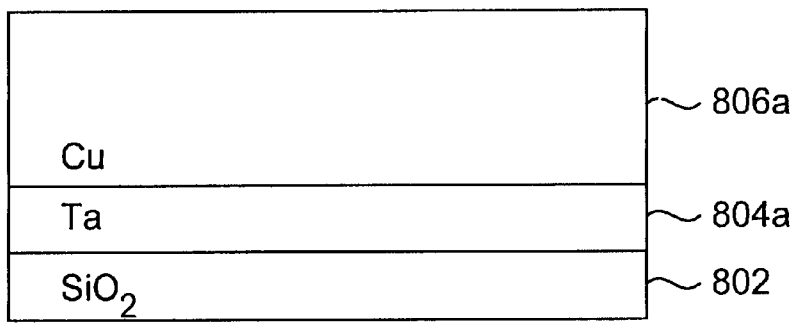
FIG. 8A illustrates three layers of a sample: a silicon dioxide layer, a Ta layer, and a Cu layer.
Figure 8B:
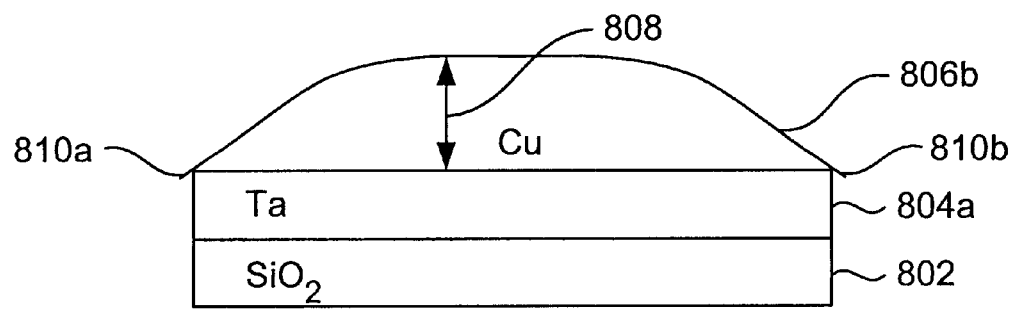
FIG. 8B illustrates the results after polishing the Cu of FIG. 8A at a relatively fast rate.
Figure 8C:
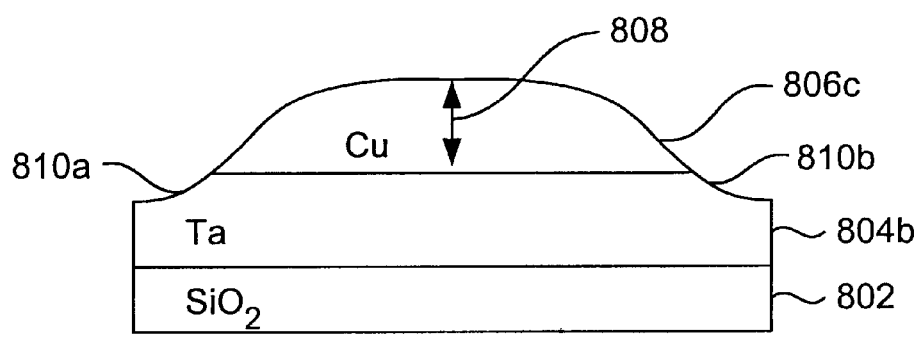
FIG. 8C illustrates dishing and erosion within the Ta layer as a result of a relatively fast rate of polishing for the Cu layer.

In another embodiment, one endpoint technique is utilized during a fast rate etch, while another is utilized during a slow rate etch. FIGS. 8A through 8C illustrate a relatively fast etch. FIG. 8A shows three layers of a sample: a silicon dioxide layer 802, a Ta layer 804a, and a Cu layer 806a. Prior to etching, the Cu layer 806a typically has a relatively large thickness as compared with the underlying Ta layer 804a.

FIG. 8B shows the results after etching the Cu at a relatively fast rate. As well known to those skilled in art, this results in an substantially uneven Cu layer 806a. For example, the Cu layer 806a may be about 1000 Å at its higher point 808. The Cu layer 806a then may taper down to a zero thickness at areas 810a and 810b. If the endpoint of the Cu layer 806 is not accurately detected, the barrier layer Ta 804b may also be etched away along the areas 810a and 810b, as shown in FIG. 8C. That is, dishing or corrosion may occur within the Ta layer 804b. Dishing and erosion are undesirable effects that occur when the Cu endpoint is not accurately detected. As a solution, the eddy current probe may be utilized to accurately detect the relatively large thickness 808 (FIG. 8B) of the Cu layer 806 before dishing occurs.

Figure 8D:
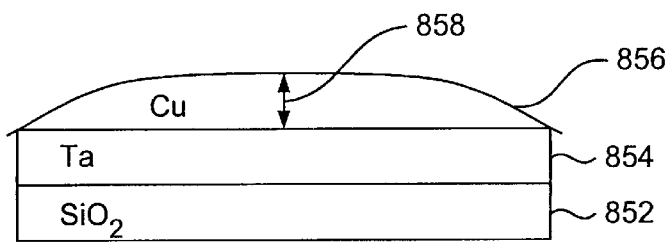
FIG. 8D illustrate a slow etch of a copper layer.

In contrast, when a relatively slow etch rate is utilized, the Cu layer 858 etches more evenly, as illustrated in FIG. 8D. For example, the Cu layer may be about 200 Å at its highest point 858. In this case, the optical probe can be utilized to accurately measure the Cu endpoint, which occurs at a relatively low Cu thickness (e.g., 200 Å).

Figure 9:
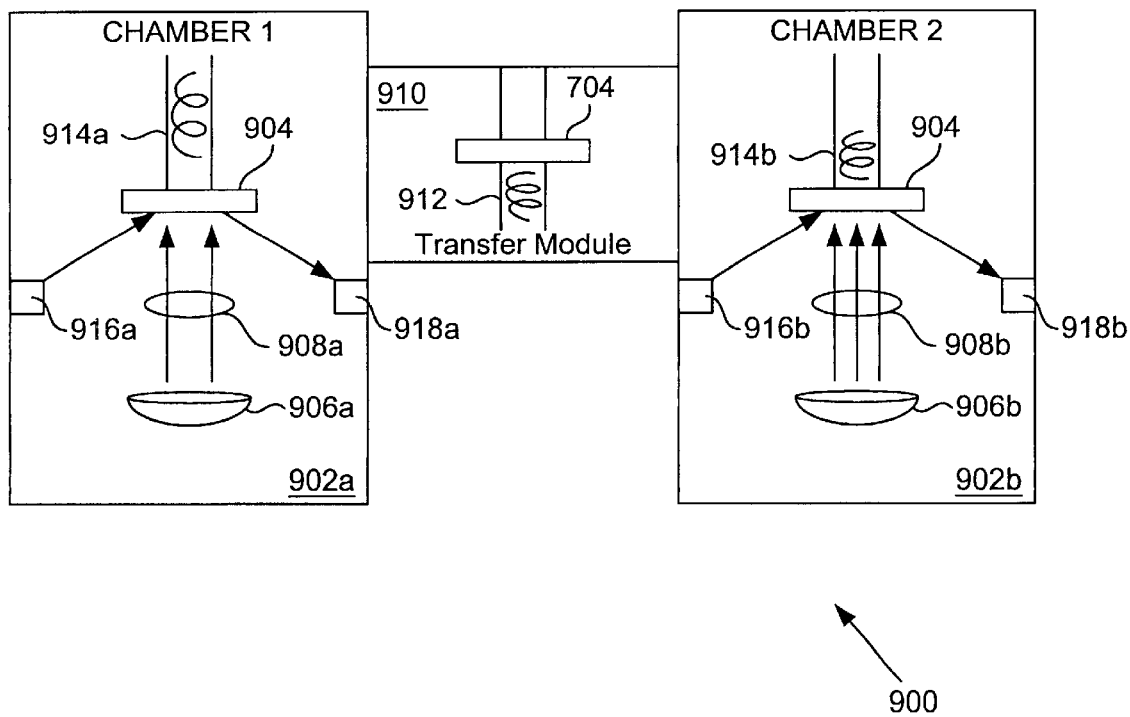
FIG. 9 is a diagrammatic illustration of a multi-chamber deposition tool having a combination eddy current and optical probe in accordance with one embodiment of the present invention.

The above described combination of measurement probes may be utilized in any other suitable in-situ tool. For example, both tools may be utilized within a deposition tool. FIG. 9 is a diagrammatic illustration of a multi-chamber deposition tool 900 having a combination eddy current and optical probe in accordance with one embodiment of the present invention.

As shown, the deposition tool 900 has a first chamber 902a and a second chamber 902b. Of course, any number and type of chambers may be used. The first chamber 902a may be used to deposit a first layer on sample 904, and the second chamber 902b is then used to deposit a second layer on sample 904. In general terms, the sample 904 is mounted over a first material 906a within the first chamber 902a. The first material 906a is evaporated onto the sample (908a).

As shown, the eddy probe 914a may be mounted on the backside of the sample 904 to detect the first layer thickness. The eddy probe 914a is preferably capable of measuring the first layer thickness through the sample's backside. Additionally, an optical emitter 916a and detector 918a may be mounted within the first chamber 902a. The emitter 916a emits a signal towards the sample, which signal is reflected from the sample 904 onto detector 918a.

The second chamber 902 may be similarly configured. As shown, the second chamber 902b also includes a second material 906b which is evaporated onto the sample 904 (908b). The second chamber 902b also includes an eddy probe 914b and optical emitter/detectors 916b and 918b.

The optical emitter/detector is optional, and the deposition tool may simply include the eddy probes. Preferably, the calibration techniques described above and/or the Mallory Patent are implemented with the eddy probes.

Rather than mount the eddy probe in each chamber, a single eddy probe may be mounted within transfer module 910. As shown, an eddy probe 912 is placed adjacent to sample 904. Thus, as the sample moves between chambers, the film thickness may then be measured. If it is determined that the film thickness is inadequate, the sample may the returned to a chamber for reapplication of the film. Of course, each probe is also coupled with a processing device (not shown) for determining film thickness.

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention.

For example, the optical measurements may also be calibrated with the film being removed. After copper is significantly polished but still optically opaque, it appears substantially like an ideal copper mirror. This copper mirror may then be utilized to adjust for changes in environmental conditions, such as a fiber being bent. Additionally, a low value reflectivity object may also be periodically positioned within the optical path to provide a low reflectivity reference for calibration.

The above eddy probe techniques may also be utilized to simply detect the sample's presence. A piezo sensor may also be embedded within the carrier, pad, or platen to determine polishing dynamics. For example, since a different sound is produced when the sample is sliding off the carrier, this slippage may be detected with the piezo sensor. By way of another example, the optical system may be mounted within an endoscopy type arrangement within an orbital platen. Additionally, a conductive polymer contact may be mounted in the pad to non-destructively obtain various electrical measurements of the sample, such as sheet resistance.

The optical and eddy probe sensors may also be used together to provide self-calibration. For example, the optical probe may be calibrated by using a metal mirror surface as a reference. A metal will be a suitable mirror-like surface when the metal layer is almost clear and still optically opaque. This point may be determined by the eddy probe. Additionally, the optical measurement device may be used to determine when a film is cleared and then to calibrate the eddy probe for making substrate resistivity measurements, instead of film resistivity measurements.

Accordingly, the present embodiments are to be considered as illustrative and not restrictive, and the invention is not to be limited to the details given herein, but may be modified within the scope and equivalents of the appended claims.

What is claimed is:

1. A method of obtaining information in-situ regarding a film of a sample using an eddy probe dung a process for removing the film, the eddy probe having first and second sensing coils, the method comprising:

(a) applying an AC voltage to the first and second sensing coils of the eddy probe;

(b) measuring one or more first signals in the first sensing coil of the eddy probe when the sensing coil is positioned proximate the film of the sample;

(c) measuring one or more second signals in the second sensing coil of the eddy probe when the sensing coil is positioned proximate to a reference material having a fixed composition and/or distance from the second sensing coil;

(d) calibrating the first signals based on the second signals so that undesired gain and/or phase changes within Me first sills are corrected; and (e) deter a property value of the turn based on the calibrated first signals, wherein the measuring one or more first signals and the measuring one or more second signals are performed substantially simultaneously.

2. A method as recited in claim 1, wherein the property value is a thickness value.

3. A method as recited in claim 2, wherein the thickness value of the film is determined by:

correlating a plurality of magnitude values with a plurality of thickness values, at least one of the magnitude values being obtained from one or more samples having known a thickness value; and matching a magnitude of the calibrated first signal with a selected one of the correlated magnitude values, wherein the thickness value of the film is determined to be the thickness value correlated with the matching correlated magnitude value.

4. A method as recited in claim 3, wherein the magnitude values are correlated to thickness values by determining a linear function for each magnitude value and associated thickness value obtained from a sample having a known thickness, the linear function for each magnitude value being a function of time and the magnitude of the calibrated first signal is matched to a magnitude value and associated thickness value of the linear function.

5. A method as recited in claim 1, wherein the reference material is a sample carrier that holds the sample.

6. A method as recited in claim 1, further comprising measuring one or more third signals in one of the first and second sensing coils of the eddy probe when the one of the first and second sensing coils is not near any sample or reference materials, wherein calibration of the first signals is further based on the third signal.

7. A method as recited in claim 6, further comprising balancing the first and second sensing coils.

8. A method as recited in claim 6, wherein the calibration of the first signals results in compensation of gain and/or phase errors caused by a temperature change or a change in distance between the eddy probe and the reference material.

9. A method as recited in claim 6, wherein the first signals, second signals and third signals each include an in-phase component and a quadrature component.

10. A method as recited in claim 9, wherein the determined property value is an amount of temperature change or an amount of distance change between the first and second sensing coils and the reference material based on the first signals, second signals and third signals and the method further comprising adjusting the removal process based on the determined temperature change amount or the determined distance change amount.

11. A method as recited in claim 10, wherein the determination of the amount of temperature change is based on the relationships between the first signals, second signals and third signals and the determination of the amount of distance change is based on an amount of change within a magnitude of the third signals as a function of time.

12. A method as recited in claim 10, wherein the removal process is adjusted by replacing a pad positioned between the eddy probe and the sample.

13. A method as recited in claim 10, wherein the removal process is adjusted by altering equipment that implements the removal process.

14. A method as recited in claim 10, wherein the removal process is adjusted by setting or modifying a finish time.

15. A method as recited in claim 1, wherein a frequency of the AC voltage applied to the firs and second sensing coils is selected based on one or more factors selected from a group consisting of film composition, sensing coil size, and desired depth of a region within the film to be measured.

16. A method as recited in claim 15, wherein operations (a) though (d) are performed using a plurality of frequencies for the AC voltage applied to the first and second sensing coils.

17. A method as recited in claim 1, wherein the first signals are measured within a plurality of areas on the sample.

18. A method as recited in claim 17, wherein the determined property value is a rate of removal for each measured area of the sample based on the calibrated first signals and the method further; comprising adjusting the removal process so as to increase removal uniformity based on the determined rates of removal.

19. A method as recited in claim 18, wherein the removal process is adjusted by increasing an amount of air within an air bladder located behind the sample carrier at a position adjacent to an area of the sample that has a relatively slow determined rate of removal.

20. A method as recited in claim 18, wherein the removal process is adjusted by increasing a rate of removal for an area of the sample that has a relatively slow determined rate of removal.

21. A method as recited in claim 17, wherein the determined property value is a rate of removal for each measured area of the sample and the method further comprising:

estimating a time that remains until the film is completely removed based on the determined rates of removal; and adjusting a finish time of the removal process based on the estimated remaining time until the film is completely removed.

* * * * *

UNITED STATES PATENT AND TRADEMARK OFFICE
CERTIFICATE OF CORRECTION

PATENT NO.    : 6,433,541 B1
DATED         : August 13, 2002
INVENTOR(S)   : Lehman et al.

It is certified that error appears in the above-identified patent and that said Letters Patent is hereby corrected as shown below:

Column 5,
Line 47, change "10" to -- 110 --

Column 9,
Line 23, change "Cow" to -- CMP --

Column 17,
Line 15, change "dung" to -- during --
Line 30, change "Me" to -- the --
Line 31, change "sills" to -- signals --
Line 32, change "deter" to -- determining --
Line 32, change "turn" to -- film --

Signed and Sealed this

Twenty-fifth Day of March, 2003

JAMES E. ROGAN
*Director of the United States Patent and Trademark Office*